(12) United States Patent
Panesar et al.

(10) Patent No.: US 12,702,791 B2
(45) Date of Patent: Aug. 11, 2026

(54) REDUCED-SPILL HYDROPHILIC CATHETER PRODUCT WITH FOAMED HYDRATION LIQUID

(71) Applicant: Hollister Incorporated, Libertyville, IL (US)

(72) Inventors: Satwinder S. Panesar, Foxford (IE); Shane O'Malley, Ballina (IE); Vivienne McNulty, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 373 days.

(21) Appl. No.: 18/253,188

(22) PCT Filed: Nov. 2, 2021

(86) PCT No.: PCT/US2021/057656

§ 371 (c)(1),
(2) Date: May 16, 2023

(87) PCT Pub. No.: WO2022/108750

PCT Pub. Date: May 27, 2022

(65) Prior Publication Data

US 2023/0414901 A1 Dec. 28, 2023

Related U.S. Application Data

(60) Provisional application No. 63/116,774, filed on Nov. 20, 2020.

(51) Int. Cl.
*A61M 25/00* (2006.01)

(52) U.S. Cl.
CPC ...... *A61M 25/002* (2013.01); *A61M 25/0045* (2013.01); *A61M 2025/0046* (2013.01)

(58) Field of Classification Search
CPC ........ A61M 25/002; A61M 25/00–104; A61B 50/30–39; A61F 9/0026; A61L 29/14;
(Continued)

(56) References Cited

U.S. PATENT DOCUMENTS 4,026,296 A 5/1977 Stoy et al.
4,906,237 A 3/1990 Johansson et al.
(Continued)

FOREIGN PATENT DOCUMENTS

EP 1131112 B1 2/2003
EP 1312385 B1 2/2006
(Continued)

OTHER PUBLICATIONS

International Search Report and Written Opinion for PCT/US2019/032892 dated Mar. 9, 2019.
(Continued)

*Primary Examiner* — Leslie R Deak
*Assistant Examiner* — Linnae E. Raymond
(74) *Attorney, Agent, or Firm* — Cook Alex Ltd.

(57) ABSTRACT

A reduced-spill urinary catheter product including a package containing a hydrophilic catheter and a foamed hydration liquid. The package having a void volume between the catheter and inner boundary of the package. The foamed hydration liquid having a density wherein the ratio of the density of the foamed liquid hydration medium to the volume of the void volume is less than 0.5.

20 Claims, 3 Drawing Sheets

(58) Field of Classification Search
CPC ... A61L 12/18; A61L 2103/15; A61L 2400/10
See application file for complete search history.

(56) References Cited

U.S. PATENT DOCUMENTS 5,562,652 A 10/1996 Davis
5,576,072 A 11/1996 Hostettler et al.
5,616,119 A 4/1997 Davis
5,623,043 A * 4/1997 Fost .................... C08G 77/388 528/25
5,876,663 A 3/1999 Laroussi
6,120,904 A 9/2000 Hostettler et al.
6,270,902 B1 8/2001 Tedeschi et al.
6,528,544 B2 3/2003 Stern et al.
6,629,961 B1 10/2003 Israelsson et al.
6,634,498 B2 10/2003 Kayeroed et al.
6,848,574 B1 2/2005 Israelsson et al.
6,923,936 B2 8/2005 Swanson et al.
6,986,868 B2 1/2006 Madsen
7,022,651 B1 4/2006 Lightcap, Jr. et al.
7,066,912 B2 6/2006 Nestenborg et al.
7,282,165 B2 10/2007 Williams, III et al.
7,476,223 B2 1/2009 McBride
7,569,155 B2 8/2009 Schaefer
7,766,163 B2 * 8/2010 Tanghoej ........... A61M 25/002 206/364
7,833,475 B2 11/2010 Madsen
8,133,435 B2 3/2012 Reynolds et al.
8,177,774 B2 5/2012 House
8,267,919 B2 9/2012 Utas et al.
8,608,689 B2 12/2013 Scheller et al.
8,703,048 B2 4/2014 Nielsen et al.
8,747,882 B2 6/2014 Utas et al.
8,747,911 B2 6/2014 Gupta et al.
8,871,869 B2 10/2014 Dias et al.
8,998,882 B2 4/2015 Knapp et al.
9,028,858 B2 5/2015 Nielsen et al.
9,138,510 B2 9/2015 Madsen
9,192,741 B1 11/2015 Najibi
9,220,866 B2 12/2015 Van Groningen et al.
9,408,946 B2 8/2016 Utas et al.
9,610,384 B2 4/2017 Belt et al.
9,801,979 B2 10/2017 Utas et al.
9,872,970 B2 1/2018 Sch+526 nfeldt
10,112,031 B2 10/2018 Matthiassen
10,245,355 B2 4/2019 Ingber et al.
10,328,237 B2 6/2019 Kelly et al.
10,398,161 B2 9/2019 Arne et al.
10,561,817 B2 2/2020 Hannon et al.
10,813,676 B2 10/2020 Shimko et al.
10,973,573 B2 4/2021 Asirvatham et al.
10,982,100 B2 4/2021 Aizenberg et al.
2002/0045049 A1 4/2002 Madsen
2002/0120333 A1 8/2002 Keogh et al.
2003/0065292 A1 4/2003 Darouiche et al.
2003/0124080 A1 7/2003 Kawam et al.
2003/0219475 A1 11/2003 Truong-Le
2004/0074794 A1 4/2004 Conway et al.
2004/0256264 A1 12/2004 Israelsson et al.
2005/0015076 A1 1/2005 Giebmeyer et al.
2005/0055044 A1 3/2005 Kangas
2005/0137582 A1 6/2005 Kull-Osterlin et al.
2005/0214376 A1 9/2005 Faure et al.
2006/0163097 A1 7/2006 Murray et al.
2007/0239107 A1 10/2007 Lundberg et al.
2007/0244449 A1 10/2007 Najafi et al.
2008/0142038 A1 6/2008 Kunzler et al.
2009/0012208 A1 1/2009 Madsen et al.
2009/0041727 A1 2/2009 Suzuki et al.
2009/0171317 A1 7/2009 Versi
2009/0221989 A1 9/2009 Najafi et al.
2009/0240214 A1 9/2009 Conway et al.
2010/0166809 A1 7/2010 Northey et al.
2010/0215643 A1 8/2010 Clevenger et al.
2010/0258568 A1 10/2010 Frederiksen et al.
2011/0114520 A1 5/2011 Matthison-Hansen
2011/0150961 A1 6/2011 Perry et al.
2011/0295239 A1 12/2011 Gustavsson
2012/0207853 A1 8/2012 Alimi et al.
2012/0289942 A1 11/2012 Becker et al.
2012/0316515 A1 12/2012 Terry
2013/0161208 A1 6/2013 Gustavsson
2014/0190846 A1 7/2014 Belt
2014/0271351 A1 9/2014 Nielsen et al.
2015/0065998 A1 3/2015 Nielsen et al.
2015/0238726 A1 8/2015 Terry
2015/0264935 A1 9/2015 Chang
2015/0335854 A1 11/2015 Dvarsater et al.
2016/0143944 A1 5/2016 Panicheva et al.
2016/0213880 A1 7/2016 Oflynn et al.
2017/0296609 A1 10/2017 Ellington et al.
2017/0296610 A1 * 10/2017 Ellington ................ A61K 9/06
2017/0312484 A1 11/2017 Shipley et al.
2018/0000993 A1 1/2018 Zhang
2018/0010038 A1 1/2018 Greenhill-Hooper et al.
2018/0221541 A1 8/2018 Pesika et al.
2018/0258363 A1 9/2018 Rhodes et al.
2019/0001098 A1 * 1/2019 Utas ................... A61M 25/002
2019/0083746 A1 3/2019 Murray et al.
2019/0105078 A1 4/2019 Taylor et al.
2019/0151610 A1 5/2019 Fletter
2019/0167849 A1 6/2019 Mcburney et al.
2019/0201659 A1 7/2019 Gustavsson et al.
2019/0216735 A1 7/2019 Venkatraman et al.
2019/0216985 A1 7/2019 Mcburney et al.
2019/0224384 A1 7/2019 Lundahl et al.
2019/0262647 A1 8/2019 Havelka-Rivard et al.
2019/0290805 A1 9/2019 Kumaraswamy et al.
2019/0290806 A1 9/2019 Farrell et al.
2020/0038535 A1 2/2020 Montes De Oca et al.
2020/0054795 A1 2/2020 Farrell et al.
2020/0146871 A1 5/2020 Palmer
2020/0206139 A1 7/2020 Williams et al.
2020/0222659 A1 7/2020 Schertiger et al.
2020/0338082 A1 10/2020 Ackler
2020/0345977 A1 11/2020 Hickmott et al.
2020/0391002 A1 12/2020 Hilton et al.
2020/0405919 A1 12/2020 Van Weerd
2021/0038508 A1 2/2021 Binyamin et al.

FOREIGN PATENT DOCUMENTS

EP 1312385 B2 10/2009
EP 1714665 B1 8/2011
EP 2695636 A1 2/2014
EP 2550030 B1 4/2018
EP 3071249 B1 8/2018
WO 2002100455 A1 1/2002
WO 2003087327 A2 10/2003
WO 2004075944 A2 9/2004
WO 2005014055 A2 2/2005
WO 2005117914 A2 12/2005
WO 2016033234 A1 3/2016
WO 2017001830 A1 1/2017
WO 2018022763 A1 2/2018
WO 2018028831 A1 2/2018
WO 2018029279 A1 2/2018

OTHER PUBLICATIONS

International Search Report and Written Opinion for PCT/US2019/032906 dated Oct. 14, 2019.

Castro, V. I., Craveiro, R., Silva, J. M., Reis, R. L., Paiva, A., & C. Duarte, A. R. (2018). Natural deep eutectic systems as alternative nontoxic cryoprotective agents. Cryobiology, 83, 15-26.

European Examination Report issued Oct. 20, 2021 in EP19729966.2.

* cited by examiner

REDUCED-SPILL HYDROPHILIC CATHETER PRODUCT WITH FOAMED HYDRATION LIQUID

This application is the U.S. National Stage Application of PCT Application No. PCT/US2021/057656, filed Nov. 2, 2021, which claims the benefit of U.S. Provisional Application Ser. No. 63/116,774, filed Nov. 20, 2020, the disclosure of all of which is hereby incorporated by reference in its entirety.

FIELD OF THE DISCLOSURE

This disclosure relates generally to reduced-spill/anti-spill hydrophilic urinary catheter products. More particularly, this disclosure relates to catheter products that include packages containing hydrophilic urinary catheters and foamed hydration liquid.

BACKGROUND

Intermittent catheterization is a good option for many users who suffer from a neurogenic bladder, that is, an atonic or unstable bladder associated with a neurological condition, such as diabetes, stroke, or spinal cord injury. Very often a neurogenic bladder is caused by conditions which may also result in diminished dexterity of the user.

Commonly, in intermittent catheterization single use, individually packaged, sterile catheters are used. Catheter shafts often include a hydrophilic surface treatment that becomes lubricous when hydrated to allow for easier and less traumatic insertion into and through the user's urethra.

Hydrophilic urinary catheter products include a package containing a catheter having a hydrophilic coating on the catheter shaft. The packages often contain a hydration liquid in direct contact with the hydrophilic coating wherein the hydration liquid hydrates the hydrophilic coating. When the hydrophilic coating is wetted or hydrated with a hydration liquid, it becomes extremely lubricous. The hydration liquid may be water or an aqueous solution.

One of the challenges of hydrophilic urinary catheter products is preventing spillage of the hydration liquid upon opening of the package and after the package has been opened. Accordingly, there remains a need for anti-spill hydrophilic urinary catheter products that reduce the risk of spillage of the hydration liquid from the package.

SUMMARY

In one aspect, a catheter product includes a package having an inner boundary defining a cavity of the package. A catheter located within the cavity of the package, and a void volume defined between the outer surface of the catheter and inner boundary of the package, the void volume having a volume (milliliters). A foamed liquid hydration medium, such as a foamed hydration liquid, located in the void volume, the foamed liquid hydration medium having a density (grams per milliliters). The ratio of the density of the foamed hydration liquid to the volume of the void volume is less than 0.1.

In another aspect, a method of making a catheter product that includes placing a catheter and foamed hydration liquid into a cavity of a package, wherein the foamed hydration liquid occupies a void volume of the cavity. The package is then closed. The foamed hydration liquid has a density (grams per milliliters) and the void volume has a volume (milliliters), and wherein the ratio of the density of the foamed hydration liquid to the volume of the void volume is less than 0.1

DETAILED DESCRIPTION OF THE EMBODIMENTS

The present disclosure is directed to hydrophilic urinary catheter products that utilize a foamed hydration liquid to hydrate the hydrophilic material of the catheter. The foamed liquid hydration medium, such as a foamed hydration liquid, may be placed into the package of the catheter product in a foamed state during manufacturing, or the foam state may be formed within the package after the liquid has been placed into the package and the package has been closed. The foam may dissipate prior to the packaging being opened by the user, or at least some foam may be present when the package is opened by the user.

Figure 1:
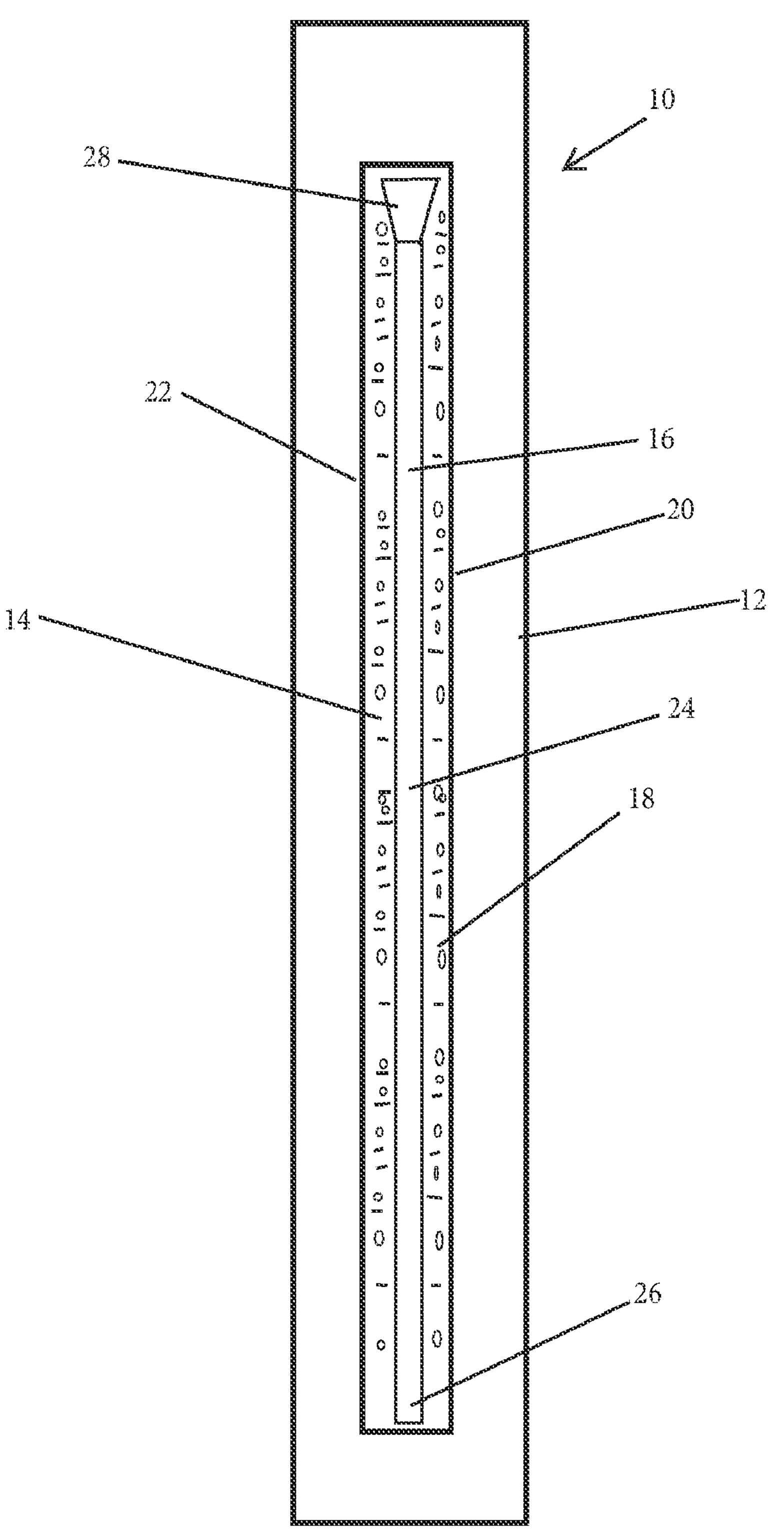
FIG. 1 is a front plan view of one embodiment of a urinary catheter product of the present disclosure.

Turning now to FIG. 1, there is shown one embodiment of a urinary catheter product 10 of the present disclosure. The product 10 includes a package 12 that has a cavity 14 containing a urinary catheter 16 and a foamed hydration liquid 18. The package 12 includes an inner boundary 20 that defines the cavity 14. For example, the package 12 may include a front wall and a rear wall that are sealed together to form the package 12. In such an embodiment the inner boundary 20 may be defined or created by the seal 22 between the front and rear walls. In alternate embodiments, the inner boundary defining the cavity may be any suitable structure of the package, such as the inner walls of a case and/or a cap.

The urinary catheter 16 includes a shaft 24 that has a hydrophilic coating thereon. The urinary catheter shaft 24 includes an insertion tip 26. A drainage member 28 is attached to the distal end of the catheter shaft 24.

The catheter product 10 includes a void volume between the outer surface of the urinary catheter 16 and the inner boundary 20 of the package. The void volume is an empty space, prior to the placement of foam in the void volume, that is exterior of the catheter. Furthermore, the void volume does not include structures of the package or other items contained in the cavity of the package. In other words, the void volume is the empty space in the cavity, prior to the placement of the foam in the void volume, that is not occupied by the catheter, structures of the package or other elements of the catheter product. Depending on the type and size of the catheter and the type and size of the package, this void volume may have a volume of between 3 ml to 100 ml. In some embodiments, the void volume may have a volume between 3 ml and 60 ml, or between 3 ml and 7 ml. In one embodiment, the void volume may have a volume of about 4 ml.

At some point between the manufacturing process and use by the end consumer, foamed hydration liquid 18 is located in this void volume. Additionally, in one embodiment the foamed hydration liquid fills the entire or substantially all of the void volume. It should be understood that the foam includes the hydration liquid and bubbles formed in or on the liquid. The foamed hydration liquid will be discussed in more detail below.

Figure 2:
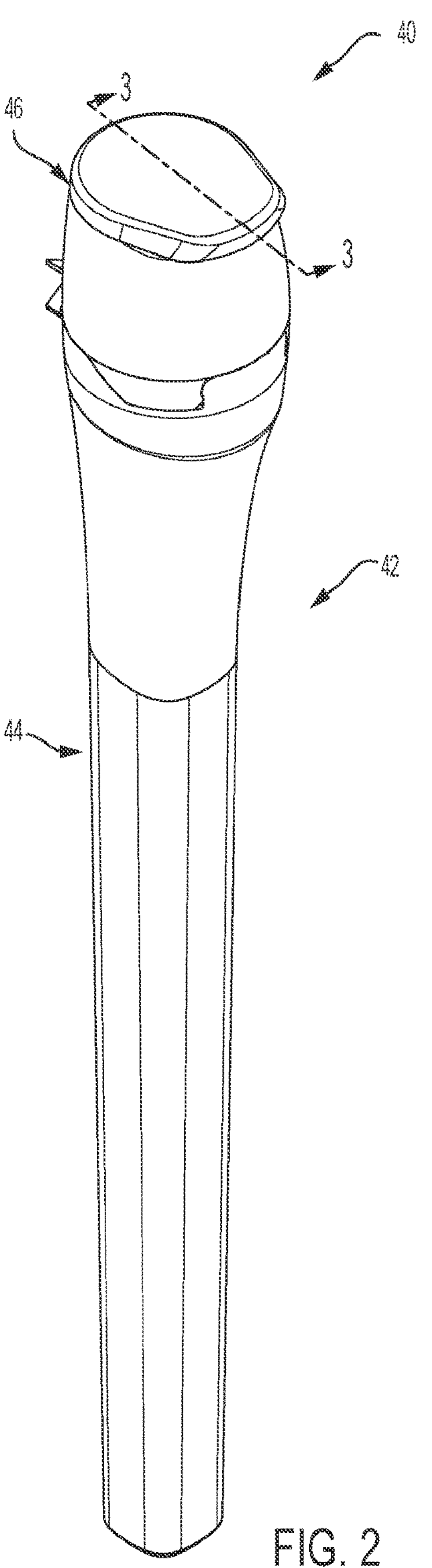
FIG. 2 is a perspective view of another embodiment of a urinary catheter product of the present disclosure.
Figure 3:
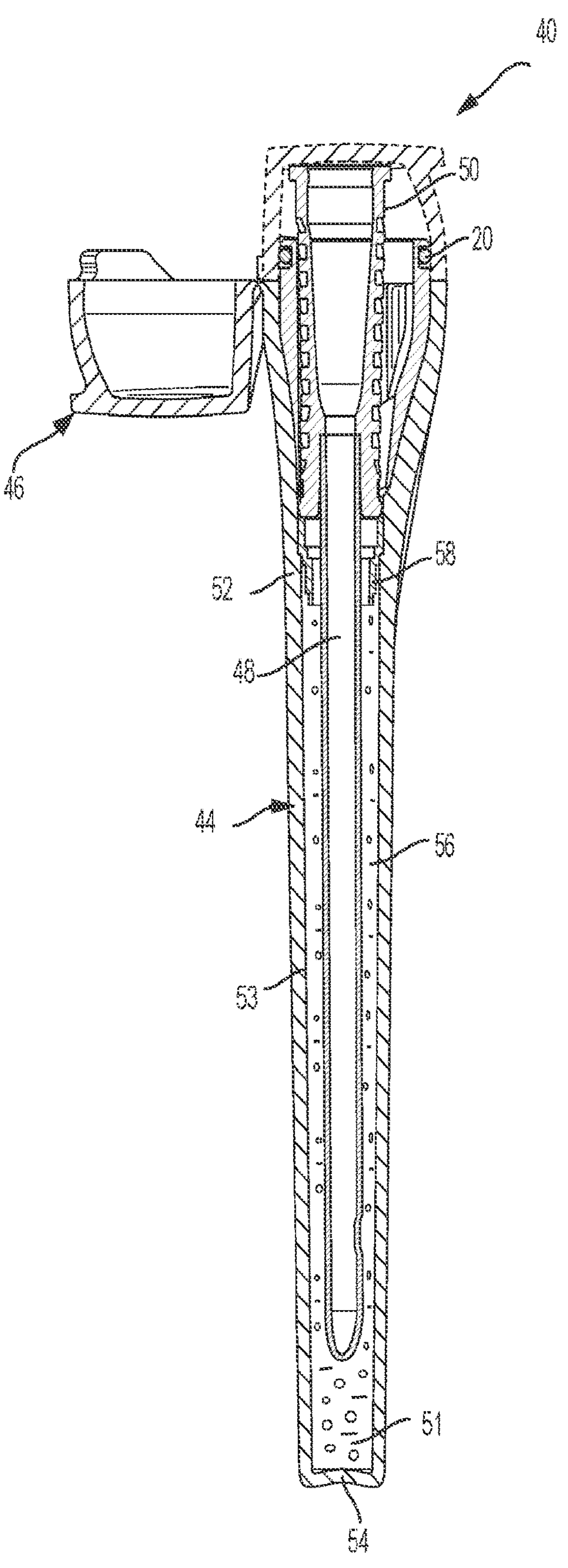
FIG. 3 is a cross-sectional view of the urinary catheter product of FIG. 2.

FIGS. 2 and 3 show another alternative of a catheter product 40 of the present disclosure. The catheter product 40 includes a package 42 that has a case 44 and cap 46. In the illustrated embodiment, the cap 46 is hinged to case 44, In other embodiments, the cap 46 may be a twist off cap. FIG. 3 also illustrates the product contained within the package 42, namely, a hydrophilic urinary catheter which includes catheter shaft 48 and a funnel 50 attached to one end of the shaft 48. Furthermore, the package 42 includes a foamed hydration liquid, such as foam 51.

The case 44 may be molded from a suitable plastic material, such as polypropylene, although other materials could be used. The case includes a tubular wall 52. The tubular wall 52 terminates at an end wall 54 that closes the bottom of the tubular wall 52. The interior surface of the tubular wall 52 may be generally cylindrical. The interior surface of the tubular wall 52 and end wall 54 serves as an inner boundary 53 that at least partially defines a cavity 56 of the package 42. Optionally, the catheter product may include a liner or insert 58 or other structures positioned within the case 44. The liner 58 may be at least partially located within cavity 56 and/or define at least a portion of the inner boundary 53 defining the cavity 56. In one embodiment, liner 58 has a shorter length than the tubular wall 52.

The catheter product 40 includes a void volume between the outer surface of the catheter shaft 48 and the inner boundary 53 of the package. Like FIG. 1, the void volume is an empty space, prior to the placement of foam in the void volume, that is exterior of the catheter shaft 48. Furthermore, the void volume does not include structures of the package or other items contained in the cavity of the package. In other words, the void volume is the empty space in the cavity, prior to placement of the foam into the void volume, that is not occupied by the catheter, structures of the package or other elements of the catheter product. In the illustrated embodiment, the void volume may be between 1 ml and 10 ml. In the illustrated embodiment, the void volume may be between 3 nil and 7 ml. In one embodiment void volume may have a volume of about 4 ml.

As mentioned above, at some point between the manufacturing process and use by the end consumer, foamed hydration liquid 51 is located in the void volume of the catheter packages. The foamed hydration liquid may be a liquid having a weight between 0.1 grams and 1 grams, or between 0.24 grams and 0.6 grams. The foamed hydration liquid may have a density between 0.05 g/ml and 0.5 g/ml, preferably between 0.06 g/ml and 0.14 g/ml. Furthermore, the ratio of the foam density (g/ml) to the volume (ml) of the void volume of the package may be between 0.005 and 0.5, preferably 0.015 and 0.0375 (foam density/void volume of package). In alternatives, the foam density to volume of void volume ratio is below 0.5, preferably below 0.0375 or below 0.03 or below 0.025. Also, in one embodiment, the volume of the void volume of the package is between 1 ml and 10 ml, preferably between 3 ml and 7 ml. For example, the volume of the void volume may be about 4 ml.

In one embodiment, the package of the catheter product includes a hydrophilic catheter and the package has a void volume having a volume of about 4 ml. The package includes a foamed hydration liquid having a density between about 0.05 g/ml and about 0.5 g/ml, preferably about 0.06 g/ml and about 0.14 g/ml. Furthermore, the liquid of the foamed hydration liquid may have a mass between about 0.1 ml to 1 ml, preferably about 0.24 ml and about 0.6 ml. In such an embodiment, after the package has been opened and turned upside down, little or no hydration liquid spillage occurs. The low foam density to void volume ratio results in little or no hydration liquid spillage. Optionally, referring to FIG. 3, the liner 58 of the package may catch or prevent any hydration liquid from spilling from the package. Accordingly, in the package shown in FIGS. 2 and 3, the combination of the low foam density to void volume ratio and the liner reduces the risk of hydration liquid spillage.

In one embodiment of making a catheter product, a hydration fluid is foamed and placed into the void volume of a package. The method may include foaming a hydration liquid that it has a density of between 0.05 g/ml and 0.5 g/ml, preferably between 0.06 g/ml and 0.15 g/ml. The package may have a void volume between 3 ml and 100 ml. In one embodiment, the package has a void volume between 3 ml and 7 ml, and in another embodiment the package a void volume of about 4 ml.

The method includes forming a hydration liquid with, for example, a mixer. In one embodiment, the hydration liquid includes:

- Water 80 wt % to 99.5 wt %, preferably 93 wt % to 98.9 wt %
- Surfactant 0.01 wt % to 5 wt %, preferably 0.025 wt % to 0.4 wt %
- Polyol 0.1 wt % to 10 wt %, preferably 1 wt % to 4.6 wt %
- Stabilizer 0.01 wt % to 2 wt %, preferably 0.05 wt % to 1 wt %
- Preservative 0.005 wt % to 0.2 wt %, preferably 0.01 wt % to 0.03 wt %

The water may be de-ionised water. The polyol may be Glycerol, PEG, pentane-diol, or the like. The surfactant may be Sodium methyl cocoyl taurate, Sodium dodecyl sulphite, or the like. The stabiliser may be xanthan gum, Karaya gum, Polyethylene Oxide or Carboxylmethyl cellulose. The preservative may be hydrogen peroxide, citric acid, or hypochlorous acid.

The hydration liquid is foamed to the above-mentioned density and the foam is placed into the package, wherein it occupies the void volume of the package. The catheter may be placed into the package before or after the foam is placed into the package. In one embodiment, the foam fills all or substantially all of the void volume of the cavity of the package.

It should be understood that various changes and modifications to the presently preferred embodiments described herein will be apparent to those skilled in the art. Such changes and modification can be made without departing from the spirit and scope of the invention disclosed herein.

What is claimed is:

1. A catheter product, comprising:

a package comprising an inner boundary defining a cavity of the package;

a catheter located within the cavity of the package;

a void volume defined between an outer surface of the catheter and inner boundary of the package, the void volume having a volume (milliliters);

a foamed liquid hydration medium located in the void volume, wherein the foamed liquid hydration medium fills the entire void volume or substantially the entire void volume, the foamed liquid hydration medium having a density (grams per milliliters); and wherein a ratio of the density of the foamed liquid hydration medium to the volume of the void volume is less than 0.5.

2. The catheter product of claim 1, wherein the ratio of the density of the foamed liquid hydration medium to the volume of the void volume is less than 0.1.

3. The catheter product of claim 1, wherein the density of the foamed liquid hydration medium is between 0.05 g/ml and 0.5 g/ml.

4. The catheter product of claim 1, wherein the density of the foamed liquid hydration medium is between 0.08 g/ml and 0.1 g/ml.

5. The catheter product of claim 1, wherein the foamed liquid hydration medium has a volume between 1 ml and 10 ml.

6. The catheter product of claim 1, wherein the foamed liquid hydration medium includes a liquid having a weight between 0.1 grams and 1 grams.

7. The catheter product of claim 1, wherein the void volume has a volume of between 3 ml and 100 ml.

8. The catheter product of claim 1, wherein the void volume has a volume of between 3 ml and 6 ml.

9. The catheter product of claim 1, wherein the void volume has a volume of 4 ml.

10. The catheter product of claim 1, wherein the foamed liquid hydration medium includes a surfactant.

11. A method of making a catheter product, comprising:

placing a catheter and foamed hydration liquid into a cavity of a package wherein a void volume of the cavity is defined between an outer surface of the catheter and inner boundary of the package, wherein the foamed hydration liquid occupies the entire void volume, or substantially the entire void volume, of the cavity;

closing the package; and wherein the foamed hydration liquid has a density (grams per milliliters) and the void volume has a volume (milliliters), and wherein a ratio of the density of the foamed hydration liquid to the volume of the void volume is less than 0.5.

12. The method of claim 11, wherein the ratio of the density of the foamed hydration liquid to the volume of the void volume is less than 0.2.

13. The method of claim 11, further including foaming a hydration liquid so as to comprise a density between 0.05 g/ml and 0.5 g/ml.

14. The method of claim 13, wherein the density of the foamed hydration liquid is between 0.08 g/ml and 0.1 g/ml.

15. The method of claim 11, wherein the foamed hydration liquid has a volume between 1 ml and 10 ml.

16. The method of claim 11, wherein the foamed hydration liquid includes a liquid having a weight between 0.1 gram and 1 gram.

17. The method of claim 11, wherein the void volume has a volume of between 3 ml and 100 ml.

18. The method of claim 11, wherein the void volume has a volume of between 3 ml and 6 ml.

19. The method of claim 11, wherein the void volume has a volume of 4 ml.

20. The method of claim 11, wherein the foamed hydration liquid includes a surfactant.

* * * * *